(12) United States Patent
Klemarczyk et al.

(10) Patent No.: US 10,662,147 B2
(45) Date of Patent: May 26, 2020

(54) PHENYLHYDRAZINE/ANHYDRIDE ADDUCTS AND ANAEROBIC CURABLE COMPOSITIONS USING SAME

(71) Applicant: Henkel IP & Holding GmbH, Duesseldorf (DE)

(72) Inventors: Philip T. Klemarczyk, Canton, CT (US); David P. Birkett, Kildare (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 318 days.

(21) Appl. No.: 15/485,546

(22) Filed: Apr. 12, 2017

(65) Prior Publication Data

US 2017/0217879 A1 Aug. 3, 2017

Related U.S. Application Data

(63) Continuation of application No. PCT/US2015/053063, filed on Sep. 30, 2015.

(60) Provisional application No. 62/067,027, filed on Oct. 22, 2014.

(51) Int. Cl.
| | | |
|---|---|---|
| C07C 243/36 | (2006.01) |
| C08F 20/18 | (2006.01) |
| C08K 5/25 | (2006.01) |
| C09K 3/10 | (2006.01) |
| C08F 20/28 | (2006.01) |
| C09J 133/10 | (2006.01) |

(52) U.S. Cl.
CPC ............ *C07C 243/36* (2013.01); *C08F 20/18* (2013.01); *C08F 20/28* (2013.01); *C08K 5/25* (2013.01); *C09J 133/10* (2013.01); *C09K 3/1006* (2013.01); *C07C 2601/14* (2017.05); *C07C 2601/16* (2017.05); *C07C 2602/42* (2017.05); *C09K 2003/1065* (2013.01); *C09K 2200/0625* (2013.01)

(58) Field of Classification Search
None
See application file for complete search history.

(56) References Cited

U.S. PATENT DOCUMENTS

| | | | |
|---|---|---|---|
| 3,218,305 A | 11/1965 | Krieble |
| 3,970,505 A | 7/1976 | Hauser et al. |
| 4,180,640 A | 12/1979 | Doherty et al. |
| 4,259,462 A | 3/1981 | Nakano et al. |
| 4,287,330 A | 9/1981 | Rich |
| 4,287,350 A | 9/1981 | Huellstrung et al. |
| 4,321,349 A | 3/1982 | Rich |
| 5,411,988 A | 5/1995 | Bockow et al. |
| 5,605,999 A | 2/1997 | Chu et al. |
| 5,811,473 A | 9/1998 | Ramos et al. |
| 6,583,289 B1 | 6/2003 | McArdle et al. |
| 6,835,762 B1 | 12/2004 | Klemarczyk et al. |
| 6,897,277 B1 | 5/2005 | Klemarczyk et al. |
| 6,958,368 B1 | 10/2005 | Klemarczyk et al. |
| 8,106,141 B2 | 1/2012 | Jacobine et al. |
| 8,362,112 B2 | 1/2013 | Birkett et al. |
| 8,481,659 B2 | 7/2013 | Birkett et al. |
| 8,598,279 B2 | 12/2013 | Messana et al. |
| 8,609,881 B2 | 12/2013 | Messana et al. |

FOREIGN PATENT DOCUMENTS

| | | |
|---|---|---|
| DE | 1 817 989 | 12/1976 |
| DE | 2 806 701 | 8/1978 |
| FR | 1581361 | 9/1969 |
| JP | 07-308757 | 11/1995 |
| WO | 99/001484 | 1/1999 |
| WO | 2008080511 | 7/2008 |

OTHER PUBLICATIONS

Iwase, Yoshiyuki. Color improvement of petroleum resin. Some components coloring petroleum resin in thermal-cracked higher fractions. Journal of Elastomers & Plastics 11(4), pp. 307-316 (1979).
RN: 1334595-78-6, STN on the Web REGISTRY database, published on Oct. 7, 2011.
RN: 477889-12-6, STN on the Web REGISTRY database, published on Dec. 31, 2020.
International Search Report issued in connection with International Patent Application No. PCT/US2015/053063 dated Feb. 4, 2016.
R.D. Rich, "Anaerobic Adhesives" in Handbook of Adhesive Technology, 29, 467-79, A. Pizzi and K. L. Mittal, eds., Marcel Dekker, Inc., New York (1994).
Krishchik et al., Reaction of Endic Anhydride with Hydrazines and Acylhydrazines. Russian Journal of Organic Chemistry, vol. 40, pp. 1140-1145 (2004).
Yang et al., A Study of the Reaction of Anti-Tricyclo [3.2.2.02,4] Nona-6-Ene-End0-8, End0-9-Dicarboxylic Anhydride with Hydrazines, The Formosan Science, vol. 44, pp. 33-50 (1991).

*Primary Examiner* — Ana Z Muresan
(74) *Attorney, Agent, or Firm* — Steven C. Bauman

(57) ABSTRACT

Phenylhydrazine/anhydride adducts and anaerobic curable compositions using these adducts are provided. The compositions are particularly useful as adhesives and sealants.

10 Claims, 5 Drawing Sheets

PHENYLHYDRAZINE/ANHYDRIDE ADDUCTS AND ANAEROBIC CURABLE COMPOSITIONS USING SAME

BACKGROUND

Field

Phenylhydrazine/anhydride adducts and anaerobic curable compositions using these adducts are provided. The compositions are particularly useful as adhesives and sealants.

Brief Description of Related Technology

Anaerobic adhesive compositions generally are well-known. See e.g. R. D. Rich, "Anaerobic Adhesives" in Handbook of Adhesive Technology, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Oftentimes, such anaerobic adhesive compositions also contain accelerator components to increase the speed with which the composition cures.

Desirable anaerobic cure-inducing compositions to induce and accelerate cure may include saccharin, toluidines, such as N,N-diethyl-p-toluidine ("DE-p-T") and N,N-dimethyl-o-toluidine ("DM-o-T"), and acetyl phenylhydrazine ("APH") together with maleic acid ("MA"). See e.g. U.S. Pat. No. 3,218,305 (Krieble), U.S. Pat. No. 4,180,640 (Melody), U.S. Pat. No. 4,287,330 (Rich) and U.S. Pat. No. 4,321,349 (Rich).

Saccharin and APH have been used as standard cure accelerator components in anaerobic adhesive cure systems since the inception of the technology. Henkel Corporation currently uses either saccharin alone or both saccharin and APH in most of its LOCTITE-branded anaerobic adhesives.

Other curatives for anaerobic adhesives include thiocaprolactam [e.g., U.S. Pat. No. 5,411,988 (Bockow)] and thioureas [e.g., U.S. Pat. No. 3,970,505 (Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-308,757 (acyl, alkyl, alkylidene, alkylene and alkyl thioureas)], certain of the latter of which had been used commercially up until about twenty years ago.

Henkel Corporation discovered a class of materials (trithiadiaza pentalenes) effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

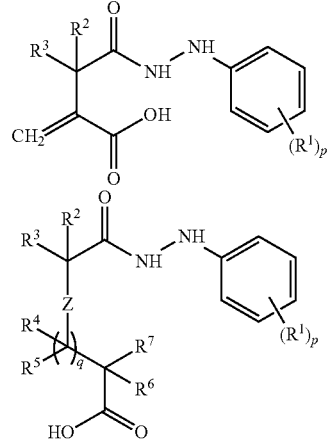

where $R^1$-$R^7$ are each independently selected from hydrogen and $C_{1-4}$; Z is a carbon-carbon single bond or carbon-carbon double bond; q is 0 or 1; and p is between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure

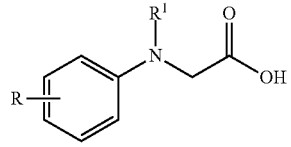

where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and alkaryl, an example of which is phenyl glycine and N-methyl phenyl glycine.

U.S. Pat. No. 6,958,368 (Messana) provides an anaerobic curable composition. This composition is based on a (meth)acrylate component with an anaerobic cure-inducing composition substantially free of saccharin and within the following structure

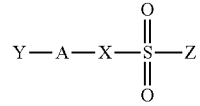

where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Three Bond Co. Ltd., Tokyo, Japan has in the past described as a component in anaerobic adhesive and sealant compositions a component called tetrahydroquinoline ("THQ"). And more recently Henkel Corporation has demonstrated the efficacy of new cure accelerators. The first class is within the structure below

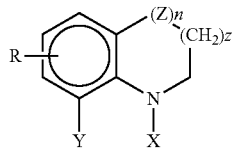

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —$NH_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —$NH_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —$NH_2$ or —SH; and n is 0 and 1 and z is 1-3, provided that when X is H, z is not 2 and is preferably 1. More specifically, THQ-based or indoline-based adducts may be embraced thereby. (See U.S. Pat. No. 8,481,659.)

The second class is within the structure below

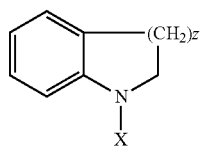

where X is $C_{1-20}$ alkyl, $C_{2-20}$ alkenyl, or $C_{7-20}$ alkaryl, any of which may be interrupted by one or more hereto atoms, and which are functionalized by at least one and preferably at least two groups selected from —OH, —$NH_2$ or —SH and z is 1-3. (See U.S. Pat. No. 8,362,112.)

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in conventional anaerobic cure inducing compositions have to one degree or another come under regulatory scrutiny, alternative components for anaerobic cure inducing compositions would be desirable. Accordingly, it would be desirable to identify new materials that function as cure components in the cure of anaerobically curable compositions.

SUMMARY

A solution to that desire is provided here. New compounds are provided, which are adducts of phenyl hydrazine and cyclic and bicyclic anhydrides. Those compounds are useful as cure accelerators for anaerobic curable compositions. The cure accelerators include the —C(=O)—NH—NH— linkage, together with a carboxylic acid functional group attached to the same molecule. For instance, the inventive cure accelerators may be within structure I:

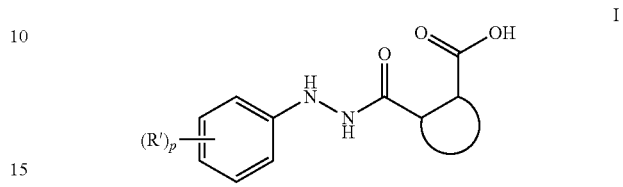

where $R^1$ is selected from hydrogen or $C_{1-4}$ alkyl; p is an integer between 1 and 5; and O represents a cycloalkyl, cycloalkenyl, bicycloalkyl or bicycloalkenyl, with or without one or more $C_{1-4}$ alkyl substituents.

The addition of these materials into anaerobic curable compositions as a replacement for some or all of the amount of conventional anaerobic cure accelerators (such as APH or the toluidines noted above) surprisingly provides at least comparable cure speeds and physical properties for the reaction products formed therefrom. In some cases, improved initial cure speed is demonstrated particularly during the early phases of cure (such as as measured after 15 minutes).

This invention also provides anaerobic curable compositions prepared with such cure accelerators, methods of preparing and using the inventive anaerobic cure accelerators as well as reaction products of the inventive anaerobic curable compositions.

As noted, certain compounds embraced by structure I are provided, including:

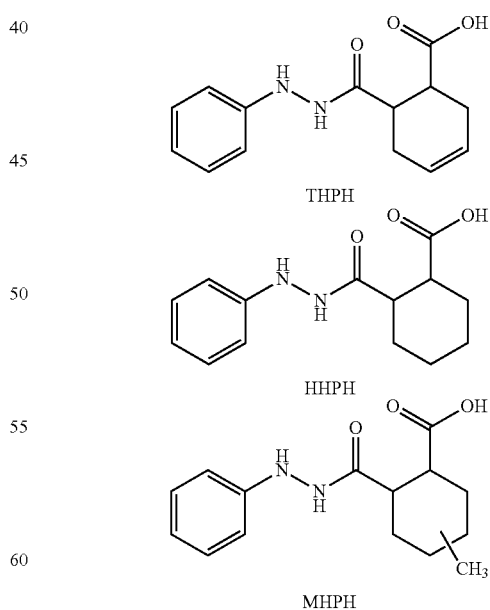

THPH represents tetrahydrophthalic phenyl hydrazine; HHPH represents hexahydrophthalic phenylhydrazine; and MHPH represents methylhexahydrophthalic phenylhydrazine.

The present invention will be more fully appreciated by a reading of the "Detailed Description", and the illustrative examples which follow thereafter.

DETAILED DESCRIPTION

Figure 1:
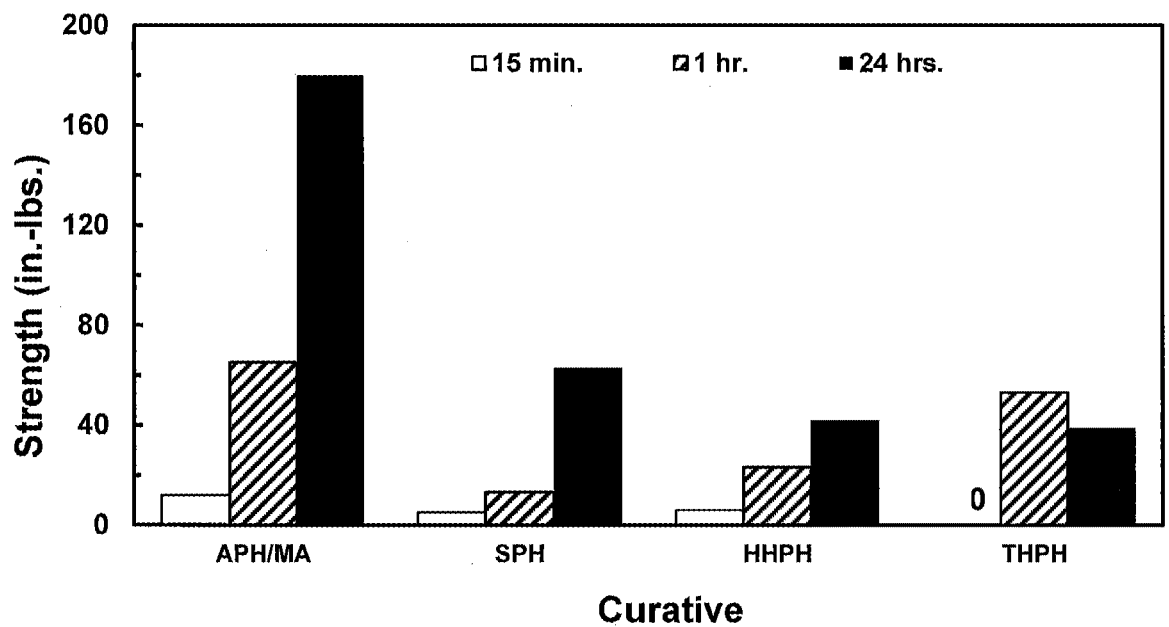
FIG. 1 depicts a bar chart, showing breakaway strength on steel nut/bolt assemblies after curing for 15 minutes, 1 hour and 24 hours, for anaerobic curable compositions based on PEGMA (Formulation 1) with one of APH/MA, SPH, THPH or HHPH as a cure accelerator.

The present invention provides anaerobic cure accelerators, having the linkage —C(=O)—NH—NH— and a carboxylic acid functional group on the same molecule. The addition of such compounds as cure accelerators into anaerobic curable compositions as a replacement for some or all of the amount of conventional cure accelerators surprisingly provides at least comparable cure speeds and physical properties for the reaction products formed.

The inventive anaerobic cure accelerators may be represented below with reference to structure I:

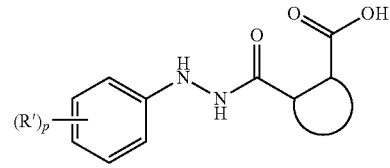

where $R^1$ is selected from hydrogen or $C_{1-4}$ alkyl; p is an integer between 1 and 5; and O represents a cycloalkyl, cycloalkenyl, bicycloalkyl or bicycloalkenyl, with or without one or more $C_{1-4}$ alkyl substituents.

Particular examples of such accelerators within structure I include:

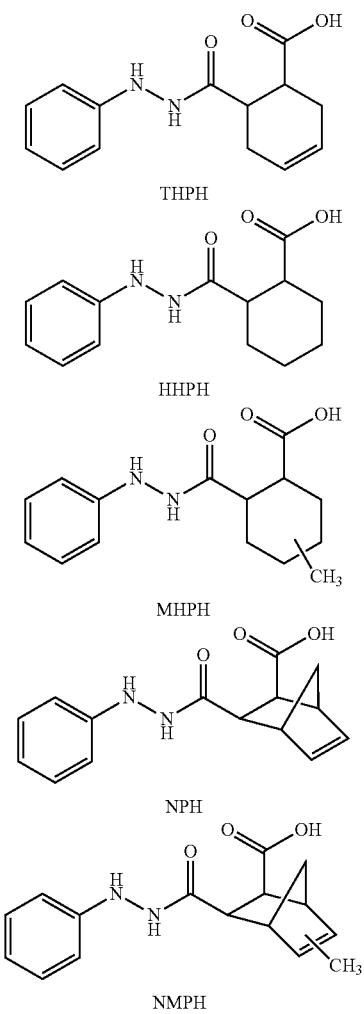

NPH represents nadic phenylhydrazine and NMPH represents nadic methyl phenylhydrazine. THPH, HHPH and MHPH are denoted above.

The inventive anaerobic cure accelerators may be prepared generally from phenyl hydrazines and anhydrides within the following respective structures:

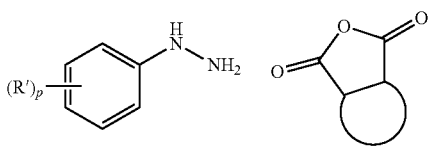

where $R^1$ is selected from hydrogen or $C_{1-4}$ alky; p is an integer between 1 and 5; and O represents a cycloalkyl, cycloalkenyl, bicycloalkyl or bicycloalkenyl, with or without one or more $C_{1-4}$ alkyl substituents. A more detailed description of the synthesis is set forth below in the examples. Specific anhydrides include:

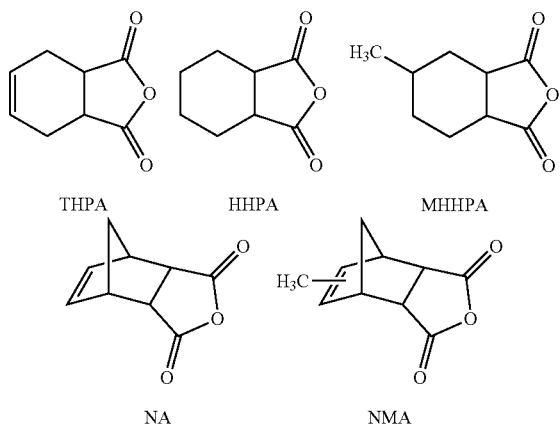

These anhydrides are tetrahydrophthalic anhydride ("THPA"), hexahydrophthalic anhydride ("HHPA"), methylhexahydrophthalic anhydride ("MHHPA"), nadic anhydride ("NA"), and nadic methyl anhydride ("NMA").

(Meth)acrylate monomers suitable for use as the (meth)acrylate component in the present invention may be chosen from a wide variety of materials, such as those represented by $H_2C=CGCO_2R^{10}$, where G may be hydrogen, halogen or alkyl groups having from 1 to about 4 carbon atoms, and $R^{10}$ may be selected from alkyl, cycloalkyl, alkenyl, cycloalkenyl, alkaryl, aralkyl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, such as di-or tri-functional (meth)acrylates like polyethylene glycol di(meth)acrylates, tetrahydrofuran (meth)acrylates and di(meth)acrylates, hydroxypropyl (meth)acrylate, hexanediol di(meth)acrylate, trimethylol propane tri(meth)acrylates, diethylene glycol dimethacrylate, triethylene glycol dimethacrylates, tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth)acrylates, ethylene di(meth)acrylates, neopentyl glycol di(meth)acrylates, and bisphenol-A mono and di(meth)acrylates, such as ethoxylated bisphenol-A (meth)acrylate, and bisphenol-F mono and di(meth)acrylates, such as ethoxylated bisphenol-A (meth)acrylate.

Still other (meth)acrylate monomers that may be used herein include silicone (meth)acrylate moieties, such as those taught by and claimed in U.S. Pat. No. 5,605,999 (Chu), the disclosure of which is hereby expressly incorporated herein by reference.

Other suitable monomers include poly(meth)acrylate esters represented by the formula:

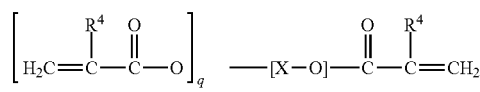

where $R^4$ is a radical selected from hydrogen, halogen or alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, such as desirably 30, and desirably about 20.

For example, X can be an organic radical of the formula:

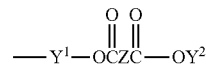

where each of $Y^1$ and $Y^2$ is an organic radical, such as a hydrocarbon group, containing at least 2 carbon atoms, and desirably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with (meth)acrylic acids, such as are disclosed in French Patent No. 1,581,361. Oligomers with (meth)acrylate functionality may also be used. Examples of useful (meth)acrylate-functionalized oligomers include those having the following general formula:

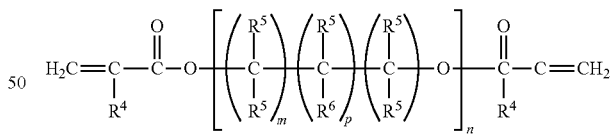

where $R^5$ represents a radical selected from hydrogen, lower alkyl of from 1 to about 4 carbon atoms, hydroxy alkyl of from 1 to about 4 carbon atoms, or

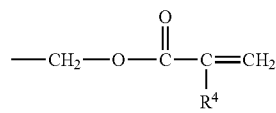

where $R^4$ is a radical selected from hydrogen, halogen, or lower alkyl of from 1 to about 4 carbon atoms; $R^6$ is a radical selected from hydrogen, hydroxyl, or

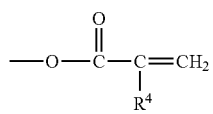

m is an integer equal to at least 1, e.g., from 1 to about 15 or higher, and desirably from 1 to about 8; n is an integer equal to at least 1, e.g., 1 to about 40 or more, and desirably between about 2 and about 10; and p is 0 or 1.

Typical examples of (meth)acrylic ester oligomers corresponding to the above general formula include di-, tri- and tetraethyleneglycol dimethacrylate; di(pentamethyleneglycol)dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

Another useful class of materials are the reaction product of (meth)acrylate-functionalized, hydroxyl- or amino-containing materials and polyisocyanate in suitable proportions so as to convert all of the isocyanate groups to urethane or ureido groups, respectively. The so-formed (meth)acrylate urethane or urea esters may contain hydroxy or amino functional groups on the nonacrylate portion thereof. (Meth) acrylate esters suitable for use have the formula

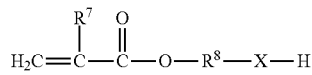

where X is selected from —O— and

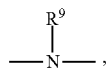

where $R^9$ is selected from hydrogen or lower alkyl of 1 through 7 carbon atoms; $R^7$ is selected from hydrogen, halogen (such as chlorine) or alkyl (such as methyl and ethyl radicals); and $R^8$ is a divalent organic radical selected from lower alkylene of 1 through 8 carbon atoms, phenylene and naphthylene. These groups upon proper reaction with a polyisocyanate, yield a monomer of the following general formula:

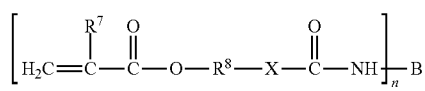

where n is an integer from 2 to about 6; B is a polyvalent organic radical selected from alkyl, alkenyl, cycloalkyl, cycloalkenyl, aryl, alkaryl, alkaryl and heterocyclic radicals both substituted and unsubstituted, and combinations thereof; and $R^7$, $R^8$ and X have the meanings given above.

Depending on the nature of B, these (meth)acrylate esters with urea or urethane linkages may have molecular weights placing them in the oligomer class (such as about 1,000 up to about 5,000) or in the polymer class (such as about greater than 5,000).

Of course, combinations of these (meth)acrylates may also be used.

The (meth)acrylate component should comprise from about 10 to about 90 percent by weight of the composition, such as about 60 to about 90 percent by weight, based on the total weight of the composition.

Recently, additional components have been included in traditional anaerobic adhesives to alter the physical properties of either the formulation or the reaction products thereof.

For instance, one or more of maleimide components, thermal resistance-conferring coreactants, diluent components reactive at elevated temperature conditions, mono- or poly-hydroxyalkanes, polymeric plasticizers, and chelators (see International Patent Application No. PCT/US98/13704, the disclosure of which is hereby expressly incorporated herein by reference) may be included to modify the physical property and/or cure profile of the formulation and/or the strength or temperature resistance of the cured adhesive. Acrylic acid may also be used in some embodiments.

When used, the maleimide, coreactant, reactive diluent, plasticizer, mono- or poly-hydroxyalkanes and/or acrylic acid, may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into the inventive compositions including, without limitation, hydroperoxides, such as cement hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. No. 4,287,350 (Rich) and U.S. Pat. No. 4,321,349 (Rich). MA is usually added to APH-containing anaerobic cure systems. One benefit of the present invention is that the inventive anaerobic cure accelerators render the use of such acids unnecessary in preparing anaerobic adhesive compositions.

Co-accelerators of free radical polymerization may also be used including aromatic sulfimides such as benzoic sulfimide (also known as saccharin). (See the '305 and the '349 patents.)

Stabilizers and inhibitors (such as phenols including hydroquinone and ketones including quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive anaerobic cure accelerators may be used in amounts of about 0:1 to about 5 percent by weight, such as about 1 to about 2 percent by weight, based on the total weight of the composition. When used in combination with conventional accelerators (though at lower levels than such conventional accelerators), the inventive accelerators should be used in amounts of 0.01 to 5 percent by weight, such as 0.02 to 2 percent by weight, based on the total weight of the composition.

Metal catalyst solutions or pre-mixes thereof are used in amounts of about 0.03 to about 0.1 percent by weight.

Other additives such as thickeners, non-reactive plasticizers, fillers, toughening agents (such as elastomers and rubbers) and other well-known additives may be incorporated therein where the art-skilled believes it would be desirable to do so.

The present invention also provides methods of preparing and using the inventive anaerobic adhesive compositions, as well as reaction products of the compositions.

The compositions of the present invention may be prepared using conventional methods which are well known to those persons of skill in the art. For instance, the components of the inventive compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. The compositions of this invention demonstrate particularly good bond strength on steel, brass, copper and zinc. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

In addition, the invention provides a method of preparing an anaerobic curable composition, a step of which includes mixing together a (meth)acrylate component, an anaerobic cure inducing composition substantially free of acetyl phenyl hydrazine and optionally substantially free of maleic acid, and an anaerobic cure accelerator compound, having the linkage —C(=O)—NH—NH— and a carboxylic acid functional group on the same molecule.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, compounds having the linkage —C(=O)—NH—NH— and a carboxylic acid functional group on the same molecule.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

Certain compounds embraced by structure I are provided, including:

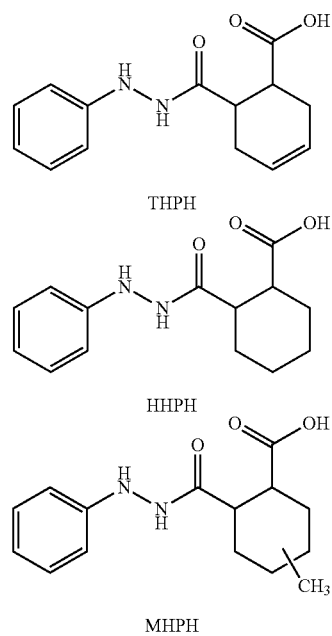

In view of the above description, it is clear that a wide range of practical opportunities is provided. The following examples are provided for illustrative purposes only, and are not to be construed so as to limit in any way the teaching herein.

EXAMPLES

An investigation was performed to evaluate certain cyclic and bicyclic anyhydride/phenylhydrazines compounds, as replacements for APH in anaerobic curable compositions, particularly adhesives.

Phenyl hydrazine, tetrahydrophthalic anhydride THPA, HHPA, MHHPA, NA, and NMA, PEGMA, MA, acrylic acid ("AA"), saccharin, and APH were purchased from the Aldrich Chemical Company.

Four cyclic and bicyclic anyhydride/phenylhydrazine compounds were prepared and evaluated to determine whether inclusion thereof would obviate the use of a separate cure component in the anaerobic adhesives.

The inventive anaerobic cure accelerators were prepared in accordance with the synthetic scheme as described below.

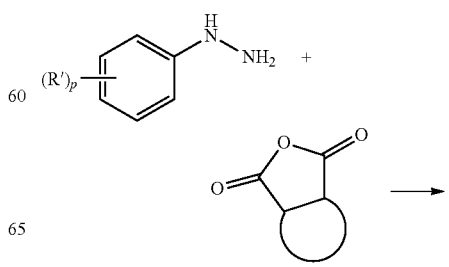

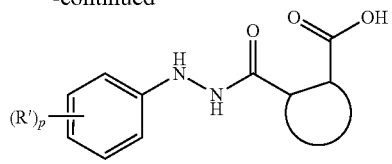

where $R^1$ is selected from hydrogen or $C_{1-4}$ alky; p is an integer between 1 and 5; and O represents a cycloalkyl, cycloalkenyl, bicycloalkyl or bicycloalkenyl, with or without one or more $C_{1-4}$ alkyl substituents.

Proton and Carbon Nuclear Magnetic Resonance ("$^1$H and $^{13}$C NMR") analyses were performed using a Varian 300 Hz Gemini Spectrophotometer. Infrared ("IR") spectral analyses were performed on neat samples using an ATI Mattson Genesis series FTIR. Melting points were obtained on a TA Instrument 2920 Differential Scanning calorimeter.

A. General Procedure for the Synthesis of Cyclic and Bicyclic Anhydride/Phenylhydrazine Compounds

HHPH

To a 1000 mL four-neck round bottom flask, equipped with a condenser, thermocouple, mechanical stirrer, an addition funnel, and a nitrogen inlet, was added HHPA (77.8 g, 0.505 mol), and $CH_3CN$ (500 mL) with stirring. The solution was heated to reflux. Phenylhydrazine (54.0 g, 0.50 mol) was added dropwise over a period of time of about 15-20 minutes, and the reaction was stirred at reflux for a period of time of 30 minutes. The product precipitated from solution on cooling to ambient temperature. Crude Yield=107.0 g (81%); Melting point=152° C. The product was recrystallized from $CH_3CN$. Crystallized Yield=77.1 g (59%): $^1$H NMR ($d_6$-DMSO) δδ 12.0 (s, 1, OH), 9.5 (s, 1, NH), 7.6 (s, 1, NH), 7.1 (t, 2, Ar—H), 6.7 (m, 3, Ar—H), 2.8 (m, 1, CO—CH), 2.6 (m, 1, CO—CH), 1.1-2.1 (m, 8, $CH_2$); $^{13}$C NMR ($d_6$-DMSO) 175, 173, 148, 128, 118, 112, 42, 28, 25, 24, 22; IR (neat) 2928, 1698, 1665, 1602, 1495, 1265, 1239, 750, 690 $cm^{-1}$.

THPH

The same procedure as above was used with THPA (76.8 g, 0.505 mol). Crude Yield=85.8 (66%); Melting point=149° C. The product was recrystallized from $CH_3CN$. Crystallized Yield=53.9 g (41%): $^1$H NMR ($d_6$-DMSO) δδ 12.1 (br s, 1, OH), 9.5 (s, 1, NH), 7.7 (s, 1, NH), 7.1 (m, 2, Ar—H), 6.7 (m, 3, Ar—H), 5.6 (m, 2, HC=CH), 2.9 (m, 2, CO—CH), 2.1-2.6 (m, 4, =C—$CH_2$—); $^{13}$C NMR ($d_6$-DMSO) 175, 173, 150, 128, 126, 125, 118, 38, 27, 26, 22; IR (neat) 3276, 1704, 1633, 1601, 1494, 1258, 1211, 921, 749, 690 $cm^{-1}$.

B. Adhesive Formulations with Cyclic and Bicyclic Anhydride/Phenylhydrazine Compounds THPH and HHPH were evaluated as anaerobic adhesive curatives in two model anaerobic adhesive compositions on degreased mild steel nuts and bolts, stainless steel nuts and bolts, and mild steel pins and collars, with APH/maleic acid and succinic phenylhydrazine ("SPH") as controls.

Model formulations, which were used for the adhesive strength evaluations, are summarized in Table A. The formulations were prepared from the noted components in the listed amounts, by mixing with a mechanical stirrer in glass vials. Each sample included a chelator and naphthaquinone as stabilizers.

TABLE A

| Materials | Formulation No./Amt (phr) | |
| --- | --- | --- |
| | 1 | 2 |
| PEGMA | 100 | 100 |
| Menadione | 0.42 | 0.42 |
| Chelator | 2.1 | 2.1 |
| Saccharin | 1.05 | 1.05 |
| TMBP-L (peroxide) | 0.9 | 0.9 |
| Acrylic acid | — | 5 |
| Phenylhydrazine/anhydride curative | Equimolar amounts 0.25-0.60 | Equimolar amounts 0.25-0.60 |

C. Physical Properties

These new cure systems were compared with control formulations containing the conventional cure components, APH/MA and saccharin, by 82° C. accelerated stability, and 15 minute/one hour/24 hour adhesion tests on nut/bolt and pin/collar specimens.

Shelf Life Stability

The 82° C. stability of the formulations was determined according to an evaluation in which the formulation is judged to have acceptable shelf stability if the adhesive formulation remains liquid for 3.5 hours or longer at 82° C. As seen from Table B below, each formulation remained liquid for greater than 24 hours.

TABLE B

| Curative | Formulation 1 | Formulation 2 |
| --- | --- | --- |
| APH/MA | >24 | >24 |
| SPH | >24 | >24 |
| THPH | >24 | >24 |
| HHPH | >24 | >24 |

The formulations thus demonstrated acceptable shelf life stability.

15 Minute, One Hour and 24 Hour Break and Prevail Strengths, and Tensile Strengths For the break/prevail adhesion tests, the specimens were cured at ambient temperature for 15 minutes, 1 hour and 24 hours after assembly and were tested as follows.

Ten nut and bolt specimens of steel and stainless steel (having been deprimed) were assembled in the same manner as for the torque test for each formulation. The break and prevail torque strengths were then recorded for half of the specimens after one hour at ambient temperature and after 24 hours at ambient temperature for the remaining specimens. The torque strengths were measured on a calibrated automatic torque analyzer.

Adhesive strength data for the phenylhydrazine curatives in Formulation 1 are given in Tables 1-4 below and shown graphically in FIGS. 1-4.

TABLE 1

| | 15 min. | 60 min. | 24 hrs. |
| --- | --- | --- | --- |
| APH/MA | 12 | 65 | 180 |
| SPH | 5 | 13 | 63 |
| HHPH | 6 | 23 | 42 |
| THPH | 0 | 53 | 39 |

TABLE 2

|  | 15 min. | 60 min. | 24 hrs. |
|---|---|---|---|
| APH/MA | 2 | 145 | 218 |
| SPH | 5 | 119 | 222 |
| HHPH | 5 | 140 | 166 |
| THPH | 0 | 150 | 215 |

TABLE 3

|  | 15 min. | 60 min. | 24 hrs. |
|---|---|---|---|
| APH/MA | 6 | 10 | 26 |
| SPH | 0 | 26 | 29 |
| HHPH | 0 | 26 | 8 |
| THPH | 12 | 22 | 23 |

TABLE 4

|  | 15 min. | 60 min. | 24 hrs. |
|---|---|---|---|
| APH/MA | 3 | 117 | 215 |
| SPH | 0 | 58 | 171 |
| HHPH | 0 | 174 | 212 |
| THPH | 24 | 193 | 212 |

Figure 5:
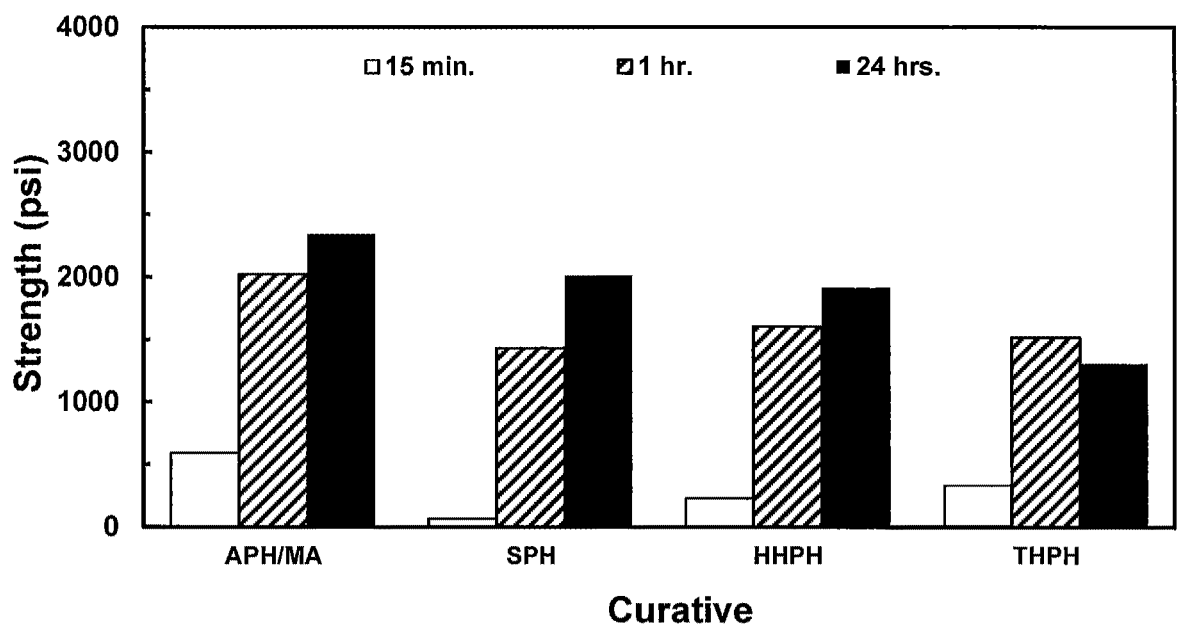
FIG. 5 depicts a bar chart, showing tensile strength on steel pin/collar assemblies after curing 15 minutes, 1 hour and 24 hours, for anaerobic curable compositions based on PEGMA (Formulation 1) with APH/MA, SPH, THPH or HHPH as a cure accelerator.

Each of these formulations was also applied to fifteen replicates of steel pins and collars (having been degreased), and maintained at ambient temperature for 15 minutes, 1 hour, and 24 hours at room temperature (25° C.) and 45-50% relative humidity, respectively. Table 5 and FIG. 5 capture the data and show the data in bar chart form.

TABLE 5

|  | 15 min. | 60 min. | 24 hrs. |
|---|---|---|---|
| APH/MA | 596 | 2022 | 2348 |
| SPH | 63 | 1428 | 2013 |
| HHPH | 229 | 1603 | 1915 |
| THPH | 332 | 1515 | 1308 |

Figure 2:
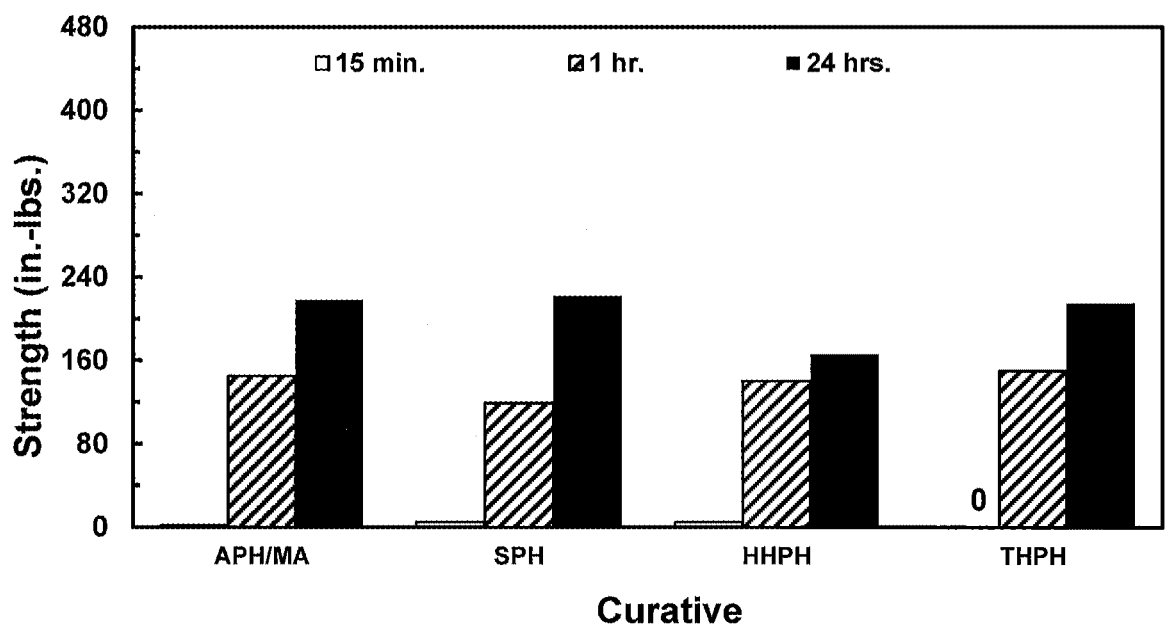
FIG. 2 depicts a bar chart, showing prevail strength on steel nut/bolt assemblies after curing 15 minutes, 1 hour and 24 hours, for anaerobic curable compositions based on PEGMA (Formulation 1) with one of APH/MA, SPH, THPH or HHPH as a cure accelerator.
Figure 3:
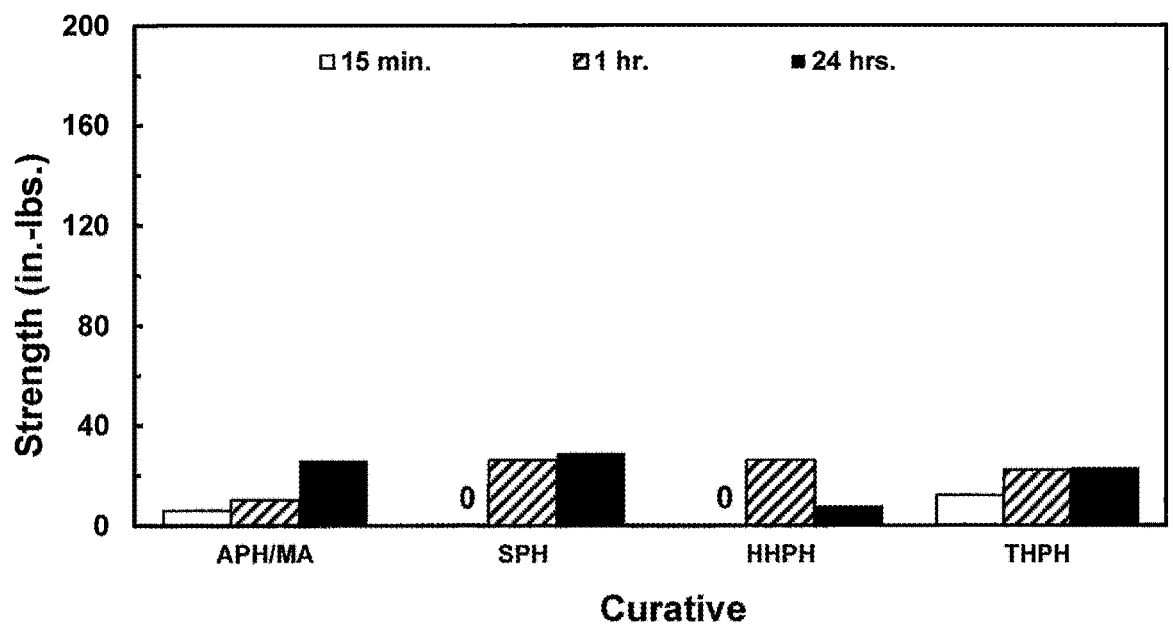
FIG. 3 depicts a bar chart, showing breakaway strength on stainless steel nut/bolt assemblies after curing for 15 minutes, 1 hour and 24 hours, for anaerobic curable compositions based on PEGMA (Formulation 1) with one of APH/MA, SPH, THPH or HHPH as a cure accelerator.
Figure 4:
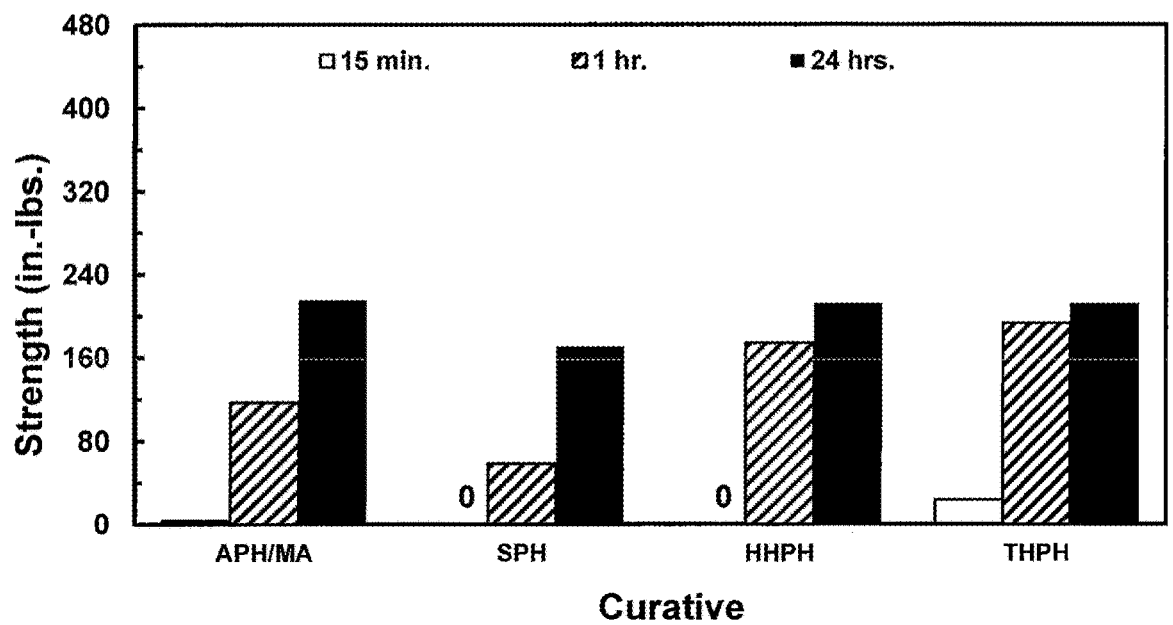
FIG. 4 depicts a bar chart, showing prevail strength on stainless steel nut/bolt assemblies after curing 15 minutes, 1 hour and 24 hours, for anaerobic curable compositions based on PEGMA (Formulation 1) with one of APH/MA, SPH, THPH or HHPH as a cure accelerator.

With reference to Tables 1-2 and FIGS. 1-2, modest improvements in strength development after curing on steel for 1 hour at room temperature may be seen with the inventive composition when contrasted to the control composition containing SPH as an accelerator. And with reference to Table 4 and FIG. 4, more significant improvements may be seen for the inventive composition after curing on stainless steel for 1 hour and 24 hours at room temperature when contrasted to the control composition.

Adhesive strength data for the phenylhydrazine based curatives in Formulation 2 are given in Tables 6-10 below and shown graphically in FIGS. 6-10.

TABLE 6

|  | 15 min. | 60 min. | 24 hrs. |
|---|---|---|---|
| APH/MA | 28 | 41 | 114 |
| SPH | 10 | 30 | 47 |
| HHPH | 44 | 38 | 77 |
| THPH | 14 | 67 | 105 |

TABLE 7

|  | 15 min. | 60 min. | 24 hrs. |
|---|---|---|---|
| APH/MA | 67 | 200 | 248 |
| SPH | 5 | 198 | 187 |
| HHPH | 122 | 178 | 205 |
| THPH | 7 | 224 | 235 |

TABLE 8

|  | 15 min. | 60 min. | 24 hrs. |
|---|---|---|---|
| APH/MA | 21 | 21 | 22 |
| SPH | 6 | 28 | 12 |
| HHPH | 27 | 9 | 13 |
| THPH | 15 | 14 | 20 |

TABLE 9

|  | 15 min. | 60 min. | 24 hrs. |
|---|---|---|---|
| APH/MA | 41 | 201 | 209 |
| SPH | 4 | 168 | 247 |
| HHPH | 40 | 247 | 206 |
| THPH | 94 | 225 | 258 |

Each of these formulations was also applied to fifteen replicates of steel pins and collars (having been degreased), and maintained at ambient temperature for 15 minutes, 1 hour, and 24 hours at room temperature (25° C.) and 45-50% relative humidity, respectively. Table 10 and FIG. 10 capture the data and show the data in bar chart form.

TABLE 10

|  | 15 min. | 60 min. | 24 hrs. |
|---|---|---|---|
| APH/MA | 1557 | 2436 | 2423 |
| SPH | 167 | 1894 | 2029 |
| HHPH | 1308 | 1947 | 2124 |
| THPH | 1253 | 1350 | 1572 |

Figure 6:
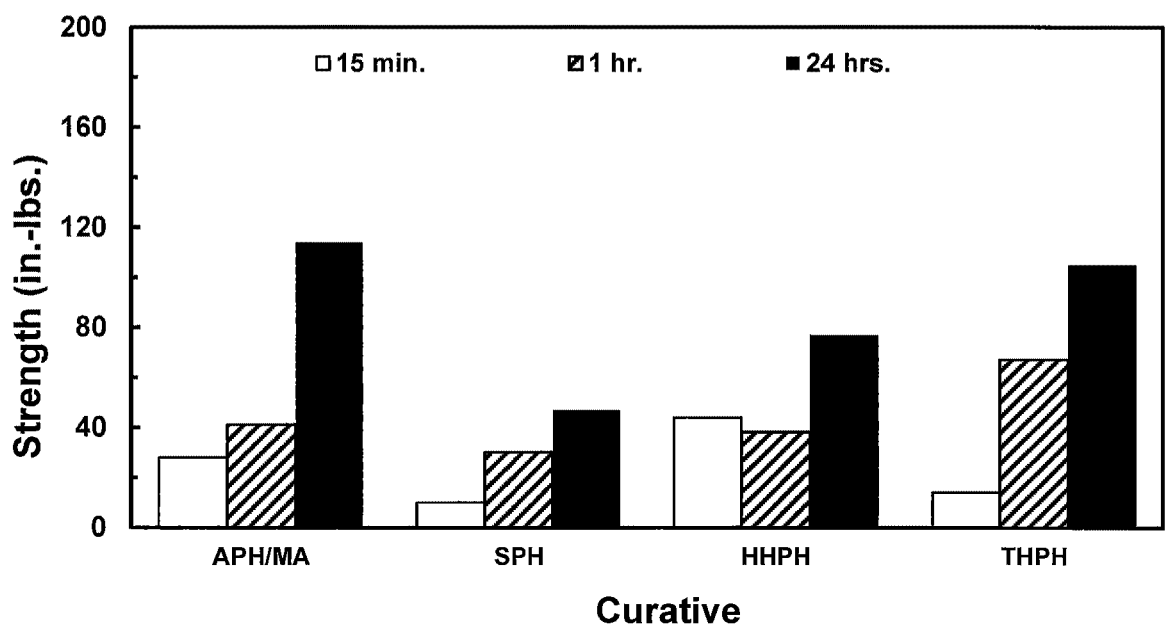
FIG. 6 depicts a bar chart showing breakaway strength on steel nut/bolt assemblies after curing for 5 minutes, 1 hour and 24 hours for anaerobic curable compositions based on PEGMA (Formulation 2) and acrylic acid with one of APH/MA, SPH, THPH or HHPH as a cure accelerator.
Figure 7:
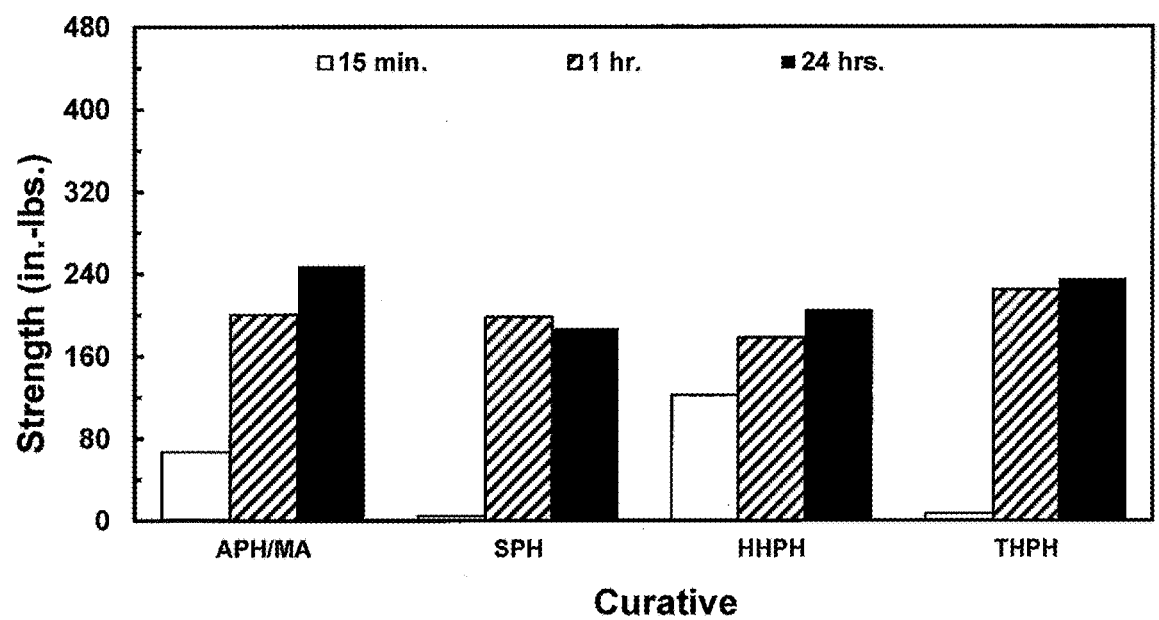
FIG. 7 depicts a bar chart showing prevail strength on steel nut/bolt assemblies after curing for 15 minutes, 1 hour and 24 hours for anaerobic curable compositions based on PEGMA (Formulation 2) and acrylic acid with one of APH/MA, SPH, THPH or HHPH as a cure accelerator.
Figure 8:
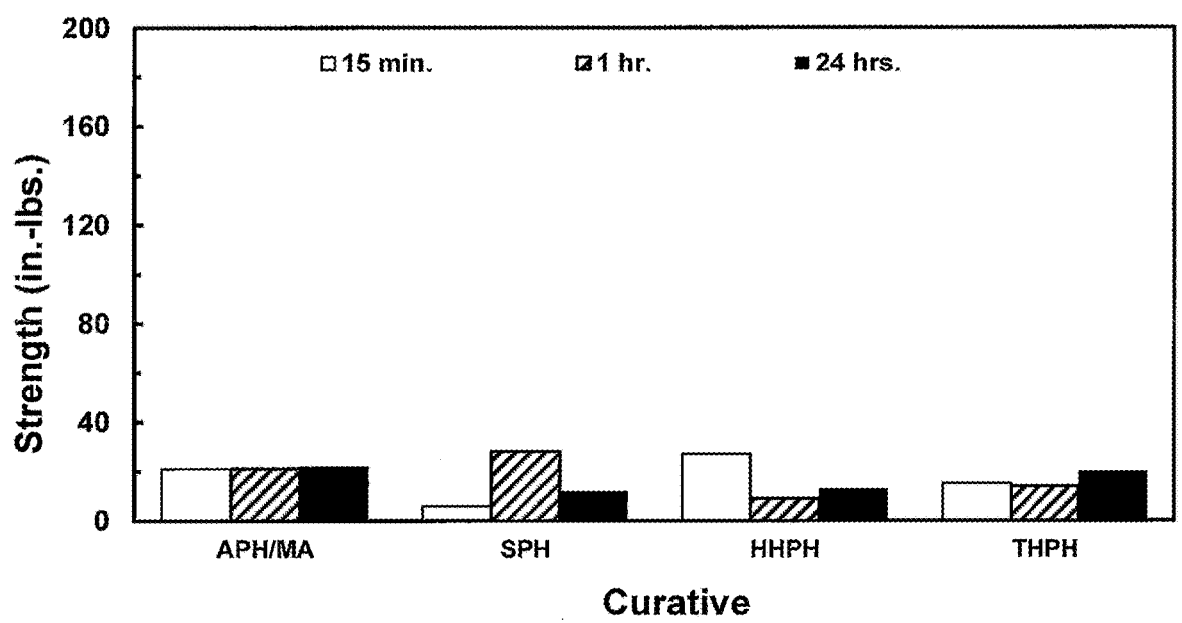
FIG. 8 depicts a bar chart showing breakaway strength on stainless steel nut/bolt assemblies after curing for 5 minutes, 1 hour and 24 hour for anaerobic curable compositions based on PEGMA (Formulation 2) and acrylic acid with one of APH/MA, SPH, THPH or HHPH as a cure accelerator.
Figure 9:
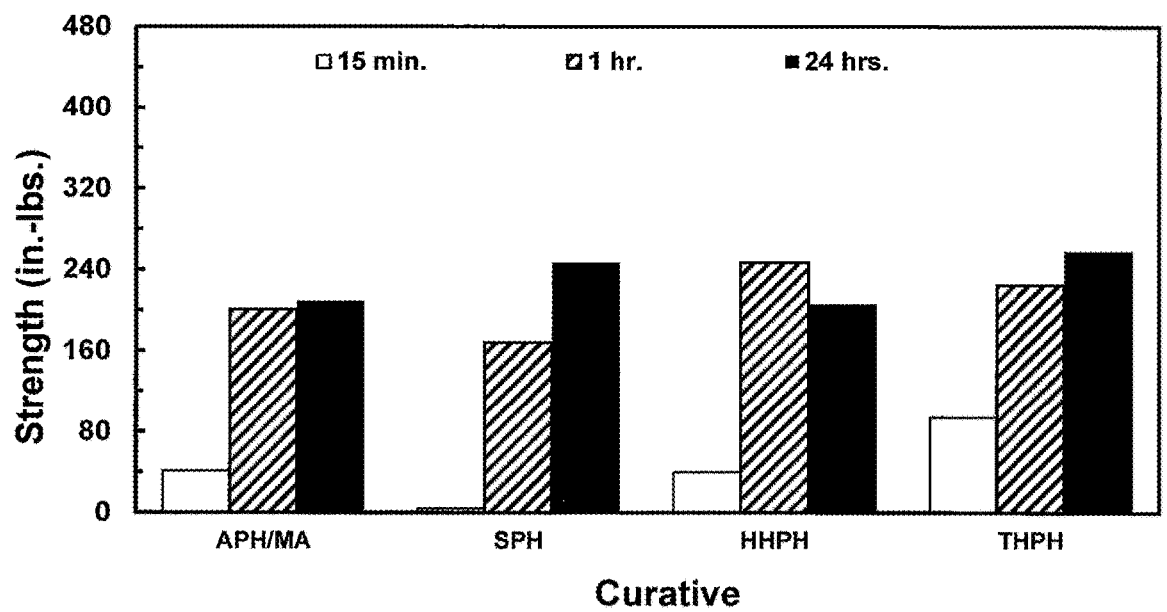
FIG. 9 depicts a bar chart showing prevail strength on stainless steel nut/bolt assemblies after curing for 15 minutes, 1 hour and 24 hours for anaerobic curable compositions based on PEGMA (Formulation 2) and acrylic acid with one of APH/MA, SPH, THPH or HHPH as a cure accelerator.
Figure 10:
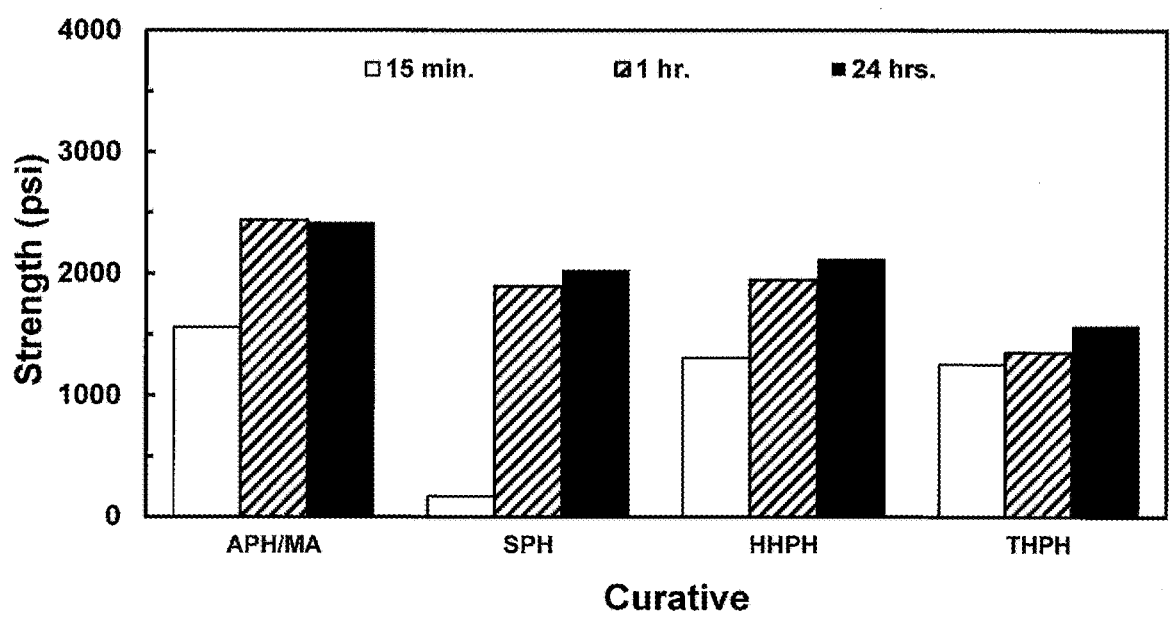
FIG. 10 depicts a bar chart showing tensile strength on steel pin/collar assemblies after curing for 15 minutes, 1 hour and 24 hours for anaerobic curable compositions based on PEGMA (Formulation 2) and acrylic acid with one of APH/MA, SPH, THPH or HHPH as a cure accelerator.

With reference to Table 6 and FIG. 6, improvement on strength development may be seen with the HHPH-containing composition as contrasted to the SPH-containing control composition when cured on steel nuts and bolts, even modestly after 15 minutes or 1 hour and significantly after 24 hours at room temperature. Table 7 and FIG. 7 show improvement in strength development with the inventive compositions as contrasted to the SPH-containing composition when cured at room temperature on steel nuts and bolts after 15 minutes. Table 9 and FIG. 9 show improvement in strength development with the inventive compositions as contrasted to the SPH-containing composition when cured at room temperature on steel nuts and bolts after 1 hour. Table 10 and FIG. 10 show improvement in strength development with the inventive compositions as contrasted to the HHPH-containing composition when cured at room temperature on steel pins and collars after 15 minutes.

What is claimed is:

1. An anaerobic curable composition, comprising: (a) a (meth)acrylate component; (b) an anaerobic cure-inducing composition and (c) a compound of Structure I

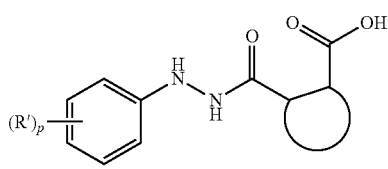

wherein:
R[1] is selected from the group consisting of H and $C_{1-4}$ alkyl;
p is an integer between 1 and 5; and
the cycloaliphatic ring represents a cycloalkyl, cycloalkenyl, bicycloalkyl or bicycloalkenyl, with or without one or more $C_{1-4}$ alkyl substituents.

2. The composition according to claim 1, wherein the compound is a member selected from the group consisting of:

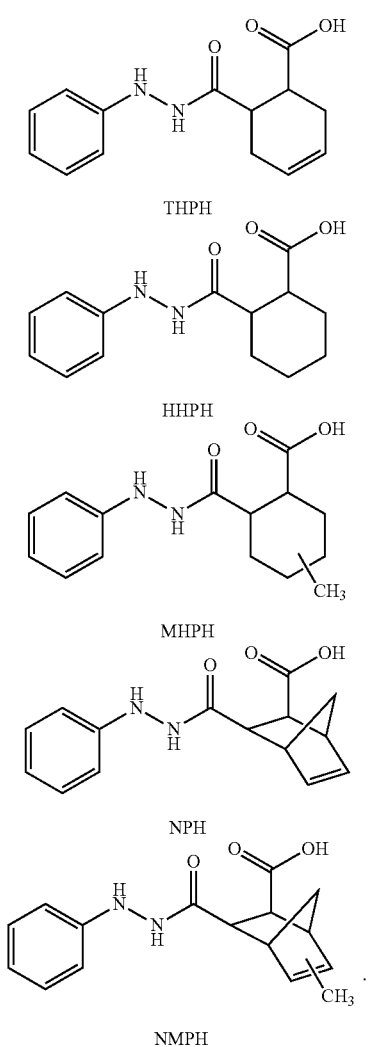

3. The composition according to claim 1, wherein the (meth)acrylate component is shown by $H_2C=CGCO_2R^{10}$, wherein G is a member selected from the group consisting of H, halogen and alkyl having from 1 to about four carbon atoms, and R[10] is a member selected from the group consisting of alkyl, cycloalkyl, alkenyl, cycloalkenyl, alkaryl, and aryl groups having from 1 to about 16 carbon atoms, with or without substitution or interruption by a member selected from the group consisting of silane, silicon, oxygen, halogen, carbonyl, hydroxyl, ester, carboxylic acid, urea, urethane, carbamate, amine, amide, sulfur, sulfonate and sulfone.

4. The composition according to claim 1, wherein the (meth)acrylate component is a member selected from the group consisting of silicone (meth)acrylates, polyethylene glycol di(meth)acrylates, tetrahydrofuran (meth)acrylates and di(meth)acrylates, hydroxypropyl (meth)acrylate, hexanediol di(meth)acrylate, trimethylol propane tri(meth)acrylates, diethylene glycol di(meth)acrylates, triethylene glycol di(meth)acrylates, tetraethylene diglycol di(meth)acrylates, diglycerol tetra(meth)acrylates, tetramethylene di(meth)acrylates, ethylene di(meth)acrylates, neopentyl glycol di(meth)acrylates, bisphenol-A-(meth)acrylates, ethoxylated bisphenol-A-(meth)acrylates, bisphenol-F-(meth)acrylates, ethoxylated bisphenol-F-(meth)acrylates, and bisphenol-A di(meth)acrylates, ethoxylated bisphenol-A-di(meth)acrylates, bisphenol-F-di(meth)acrylates, and ethoxylated bisphenol-F- di(meth)acrylates.

5. The composition according to claim 1, further comprising a co-accelerator.

6. A process for curing an anaerobic curable composition, comprising the steps of: applying an anaerobic curable composition according to claim 1, to a desired substrate surface; and exposing the composition to an anaerobic environment for a time sufficient to cure the composition.

7. A method of preparing an anaerobic curable composition, comprising the step of:
mixing together:
i) as an anaerobic cure accelerator, a compound having Structure I

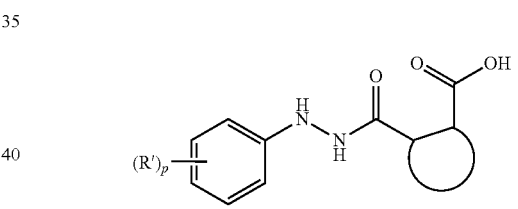

wherein:
R[1] is selected from the group consisting of H and $C_{1-4}$ alkyl;
p is an integer between 1 and 5; and
the cycloaliphatic ring represents a cycloalkyl, cycloalkenyl, bicycloalkyl or bicycloalkenyl, with or without one or more $C_{1-4}$ alkyl substituents;
(ii) a (meth)acrylate component; and
(iii) an anaerobic cure-inducing composition.

8. The composition according to claim 1, wherein the anaerobic cure-inducing composition comprises the combination of a free radical initiator and a free radical co-accelerator.

9. A method of using a compound of Structure I

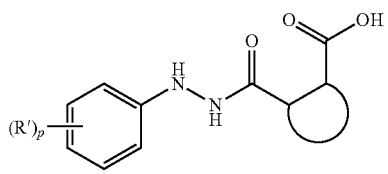

wherein:

R$^1$ is selected from the group consisting of H and C$_{1-4}$ alkyl;

p is an integer between 1 and 5; and the cycloaliphatic ring represents a cycloalkyl, cycloalkenyl, bicycloalkyl or bicycloalkenyl, with or without one or more C$_{1-4}$ alkyl substituents, as an anaerobic cure accelerator comprising the step of either: (I) mixing the compound with a (meth)acrylate component, an anaerobic cure inducing composition, or (II) applying onto a surface of a substrate the compound and applying thereover an anaerobic curable composition.

10. The composition of claim 1, further comprising acrylic acid.

* * * * *